United States Patent [19]
U'Ren

[11] Patent Number: 5,785,925
[45] Date of Patent: Jul. 28, 1998

[54] CENTRIFUGE TUBE PHASE SEPARATION PLUG

[75] Inventor: Jack U'Ren, Kirkland, Wash.

[73] Assignee: Saigene Corporation, Bothell, Wash.

[21] Appl. No.: 703,147

[22] Filed: Aug. 29, 1996

[51] Int. Cl.$^6$ ..................................................... G01N 9/30
[52] U.S. Cl. ........................... 422/72; 422/58; 422/101; 422/102; 436/177; 436/178
[58] Field of Search .......................... 422/58, 72, 100, 422/101, 102, 104; 215/320, 355; 435/288.4, 283.1; 436/178, 177

[56] References Cited

U.S. PATENT DOCUMENTS

| | | | |
|---|---|---|---|
| 4,279,863 | 7/1981 | Friehler | 422/102 |
| 4,755,356 | 7/1988 | Robbins et al. | 422/102 |
| 4,861,477 | 8/1989 | Kimura | 210/359 |
| 5,073,341 | 12/1991 | Hargreaves | 422/58 |
| 5,167,929 | 12/1992 | Korf et al. | 422/102 |
| 5,202,093 | 4/1993 | Cloyd | 422/102 |
| 5,282,981 | 2/1994 | Adams et al. | 210/789 |
| 5,308,506 | 5/1994 | McEwen et al. | 210/745 |
| 5,552,325 | 9/1996 | Nochumson et al. | 436/177 |
| 5,620,662 | 4/1997 | Perlman | 422/102 |

Primary Examiner—Harold Y. Pyon
Attorney, Agent, or Firm—Townsend and Townsend and Crew

[57] ABSTRACT

A centrifuge sample tube phase separation plug is disclosed for use in conjunction with sample tube to effect organic solvent separation on a volumetric basis. The centrifuge sample tube is of the type having a conical bottom end closed at the apex with an upward extending cylindrical portion opening to the top of the sample tube. A centrifuge sample tube cap is provided to close the sample tube with the mixed organic solvent and sample. The sample tube cap contains a plug having a central aperture and a tapered profile for fitting into the top of the conical bottom section of the centrifuge sample tube. Presuming that the sample tube is loaded and capped with mixed organic solvent and sample, centrifugation occurs. Into the centrifugation process, the plug releases from the cap and passes from the cap area, through the sample, to the top of the conical portion of the centrifuge sample tube. The plug then lodges in the sample tube at the top of the conical section fitting its tapered exterior profile to the corresponding tapered interior profile of the sample tube. By the expedient of controlling the amount of organic solvent utilized to fit below the top surface of the plug when centrifugated, convenient decanting of the sample from the solvent results.

4 Claims, 3 Drawing Sheets

CENTRIFUGE TUBE PHASE SEPARATION PLUG

This invention relates to centrifuge sample tubes. More particularly, a centrifuge sample tube is disclosed which has a phase separation plug for separating the sample from the organic phase for the convenient decanting of the sample when separation by centrifugation occurs.

BACKGROUND OF THE INVENTION

Centrifuges are used in the extraction of DNA from tissues like whole blood or homogenized biopsy samples. Typically, the tissue is placed in an organic solvent mixture such as phenol or a chloroform/phenol mixture. The sample is then placed in a centrifuge sample tube and mixed with the organic solvent. Usually, "vortexing" of the sample within the centrifuge sample tube occurs in a machine which produces a swirling motion not unlike a vortex. Once relatively complete mixing has occurred, centrifugation occurs. This leaves the heavier organic solvent at the bottom of the centrifuge sample tube, the lighter sample at the top of the centrifuge sample tube, and an interface between the organic solvent and sample. For subsequent processing, it is necessary that the sample be decanted, and the organic solvent usually discarded. Sometimes, the above process is repeated until the sample is relatively pure from proteins that will ultimately interfere with the processing and analysis of the DNA that follows.

Attempts have been directed making decanting of the sample more convenient. Most attempts have been directed at the placement of a material at the interface between the heavier organic solvent and the lighter extracted sample. Such materials have been made in the form of a gel which forms at the interface.

Unfortunately, the relative densities of both the sample and organic solvent change. When this change occurs, differing gels have to be used for differing organic solvent and sample combination.

SUMMARY OF THE INVENTION

A centrifuge sample tube phase separation plug is disclosed for use in conjunction with sample tube to effect organic solvent separation on a volumetric basis. The centrifuge sample tube is of the type having a conical bottom end closed at the apex with an upward extending cylindrical portion opening to the top of the sample tube. A centrifuge sample tube cap is provided to close the sample tube with the mixed organic solvent and sample. The sample tube cap contains a plug having a central aperture and a tapered profile for fitting into the top of the conical bottom section of the centrifuge sample tube. Presuming that the sample tube is loaded and capped with mixed organic solvent and sample, centrifugation occurs. Into the centrifugation process, the plug releases from the cap and passes from the cap area, through the sample, to the top of the conical portion of the centrifuge sample tube. The plug then lodges in the sample tube at the top of the conical section fitting its tapered exterior profile to the corresponding tapered interior profile of the sample tube. By the expedient of controlling the amount of organic solvent utilized to fit below the top surface of the plug when centrifugated, convenient decanting of the sample from the solvent results.

DESCRIPTION OF THE PREFERRED EMBODIMENT

Figure 1A:
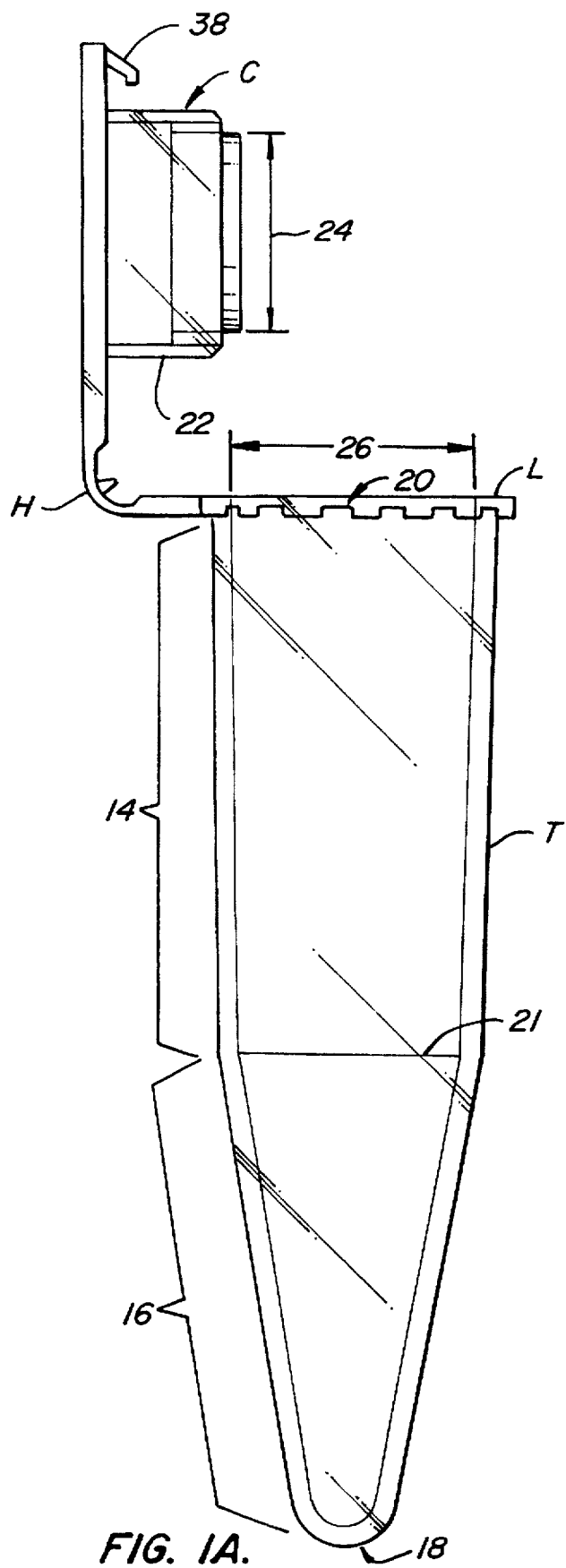
FIG. 1A is a side elevation of the centrifuge sample tube having the conical bottom section and the cylindrical upper section with the cap for holding the separation plug shown attached by a hinge at the opening of the sample tube with the phase separation plug disposed in the cap.

Referring to FIG. 1A, centrifuge sample tube T is illustrated. Centrifuge sample tube T is a standard item of manufacture having opening 20, upper cylindrical portion 14, and lower conical portion 16 closed at spherical apex 18. As is needed for mold release, upper cylindrical portion 14 is slightly tapered from boundary 21 at the upper end of lower conical portion 16.

Cap C is shown mounted by integral hinge H to lip L of centrifuge sample tube T. Cap C has cylindrical interior cap portion 22 which has outside diameter 24. Cap C at outside diameter 24 wedges into upper cylindrical portion 14 at opening 20. As will hereafter be more fully discussed, plug P wedges into cylindrical interior cap portion 22 and is held and released by cylindrical interior cap portion 22 during centrifugation. Typically, centrifuge sample tube T is integrally molded from polypropylene and includes closure hook 38 for maintaining cap C closed when contents to be mixed and centrifugated are inserted.

Figure 1B:
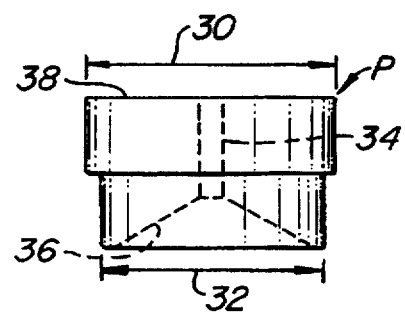
FIG. 1B is a side elevation of the plug.

Referring to FIG. 1B, plug P can be understood. Plug P has first large diameter 30 at the top. Plug P has second smaller diameter 32 at the bottom. This configuration imparts a step tapered profile to plug P which serves two purposes.

First, plug P at first large diameter 30 has sufficient dimension to wedge into outside diameter 24 of cap C. This wedging fit has sufficient frictional force to enable plug P to be held by cap C both during vortexing of the contents of centrifuge sample tube T and during the initial stages of centrifugation of centrifuge sample tube T. This frictional force is insufficient to maintain plug P during the full force of centrifugation.

Secondly, first large diameter 30 and second smaller diameter 32 cooperate when plug P falls to the top of lower conical portion 16 in the vicinity of boundary 21. Specifically, the step taper of first large diameter 30 and second smaller diameter 32 wedge into lower conical portion 16. The importance of this wedge fitting in preventing canting of plug P in centrifuge sample tube T will be described in more detail with respect to FIG. 3.

Continuing on with the description of plug P, the plug defines circular top 38 and conical bottom 36. Between circular top 38 and conical bottom 36, there is cylindrical bore 34. As will hereafter be disclosed, cylindrical bore 34 forms the decanting interface between separated materials within centrifuge sample tube T.

The density of the material from which plug P is constructed is important. Specifically, it is required that plug P have a density exceeding that of sample S. Preferably, this density exceeds the density of organic solvent O. In my preferred embodiment, I utilize Polyetheretherketone (PEEK) 30% glass filled plastic having a density of about 1.54 g/cc.

Figure 2:
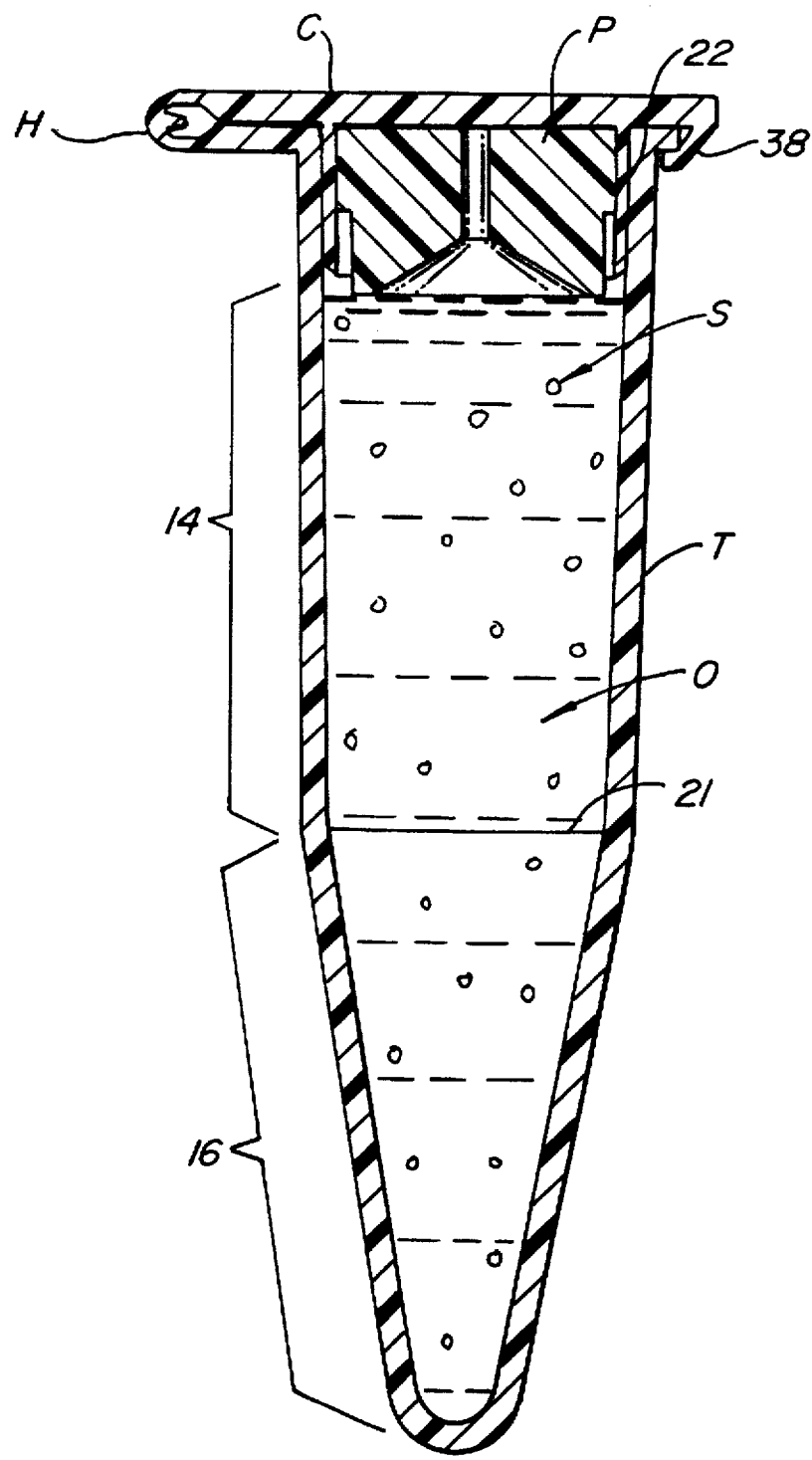
FIG. 2 illustrates the mixed sample and solvent within the centrifuge sample tube at the beginning of centrifugation with the phase separation plug lodged within the tube cap immediately before release under the forces of centrifugation; and, FIG. 3 illustrates the centrifuge sample tube of FIG. 2 within a schematically illustrated centrifuge rotor with the phase separation plug released and lodged at the top of the conical section of the centrifuge sample tube with the organic solvent below the phase separation plug and the sample above the phase separation plug.
Figure 3:
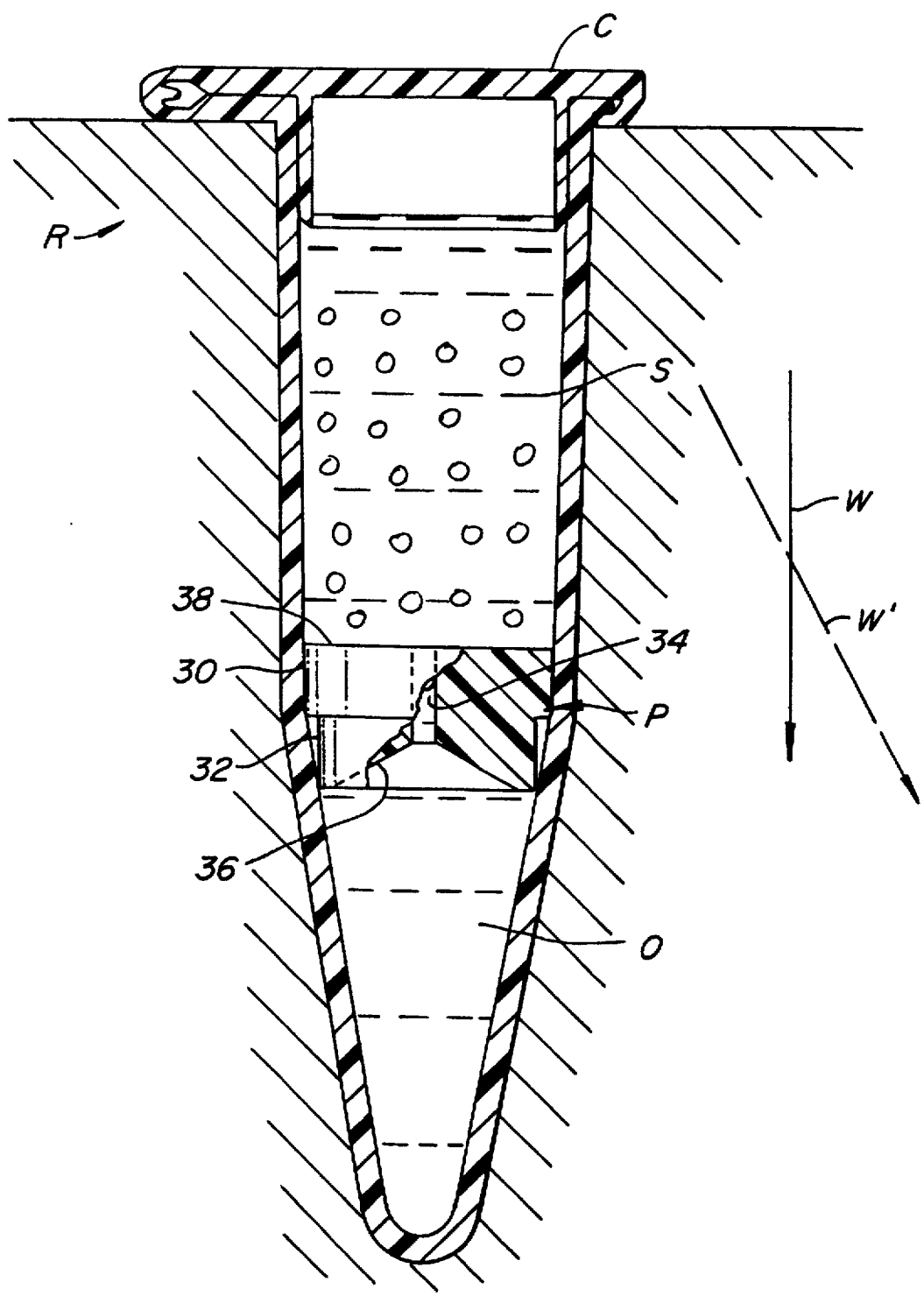

Having set forth the construction of this disclosure, operation can be understood with sequential reference to FIGS. 2 and 3.

Referring first to FIG. 2, centrifuge sample tube T is filled with organic solvent O and sample S. Two important considerations are made in this filling.

First, the amount of organic solvent O is generally sufficient to fill lower conical portion 16 of centrifuge sample tube T only. In any event, it is undesirable for a significant amount of organic solvent O to be above plug P at circular top 38 when centrifugation is completed.

Second, sample S and organic solvent O are mixed, preferably by vortexing in centrifuge sample tube T. This mixing is sufficient to cause the solvent—usually a chloroform/phenol mixture—to extract protein from the DNA present in the sample. When this mixing process is through, it is then necessary to separate by centrifugation the sample and solvent.

Referring to FIG. 3, centrifuge sample tube T is shown with plug P released from cap C. Some discussion related to this release is worthwhile.

Referring to FIG. 3, the surround of centrifuge sample tube T is shown by rotor body R. As is well known in the centrifuge arts, rotor body R can either be a so-called swinging bucket rotor or a fixed angle rotor. Rotor body R is provided with sample tube aperture A which intimately surrounds centrifuge sample tube T. The surround imparts to the sample tube sufficient strength resist the fluid forces generated during centrifugation.

Where a so-called swinging bucket rotor is utilized, forces W on the sample tube are generally parallel to the longitudinal axis of the sample tube. Where, however, a fixed angle rotor is used, canted forces W' act on the contents of centrifuge sample tube T. This is because the angle of centrifuge sample tube T is fixed—while the force W' is at an angle with respect to the longitudinal axis of centrifuge sample tube T. This can present a problem to the seating of plug P at boundary 21 between upper cylindrical portion 14 and lower conical portion 16.

Specifically, it is desired that plug P not be canted when such seating occurs. The step tapered construction of first large diameter 30 and second smaller diameter 32 prevents such canting despite canted forces W'.

The actual performance of plug P is interesting to note. In operation of a centrifuge, plug P releases with a detectable noise. This usually occurs when the centrifuge is at about ¾ speed—say 750 rpm of a top speed of about 1,000 rpm. It is believed that separation of sample S and organic solvent O occurs before plug release. However that may be, the results of the centrifugation are noted in FIG. 3.

Specifically, organic solvent O is below plug P; sample S is above plug P. Further, and dependent upon the amount of organic solvent O utilized, interface I between organic solvent O and sample S preferably resides in cylindrical bore 34 of plug P. This interface comprises a boundary, having the organic solvent on one side and the sample on the other side. By the simple expedient of opening cap C, rapid decanting of sample S can occur with usual discard of centrifuge sample tube T and the trapped organic solvent O below plug P.

What is claimed is:

1. A phase separation plug and centrifuge sample tube in combination comprising:

a centrifuge sample tube having an upper open end and a lower closed end;

the centrifuge sample tube at the lower and closed end including a lower and closed conical portion and an upper cylindrical portion defining an opening for a cap;

a cap for mounting to the centrifuge sample tube at the opening;

a plug body separated from the cap, the plug body shaped for movement under forces of centrifugation from the cylindrical portion of the sample tube to the lower and closed conical portion of the sample tube;

the plug body defining at least one passage for permitting fluid flow from the lower and closed conical portion of the plug body to the upper cylindrical portion of the plug body;

means for holding the plug body to the cap under a first force toward the lower and closed end and releasing the plug body from the cap under a second and greater force toward the lower and closed end; and, the plug body defining at a peripheral surface a profile for lodging to the lower and closed conical portion of the sample tube whereby downward movement of the plug body under the forces of centrifugation is inhibited.

2. A phase separation plug and centrifuge sample tube in combination according to claim 1 and further comprising:

the means for holding the plug to the cap includes a cylindrical skirt protruding from the cap, the cylindrical skirt having an inside diameter allowing wedging of the plug into the cylindrical shirt.

3. A phase separation plug for use in a centrifuge sample tube according to claim 1 and wherein:

the plug body has a tapered construction.

4. A phase separation plug for use in a centrifuge sample tube according to claim 3 and wherein:

the plug body has a step tapered profile.

\* \* \* \* \*